United States Patent [19]

Hirschmann et al.

[11] Patent Number: 5,250,564
[45] Date of Patent: Oct. 5, 1993

[54] AROMATIC PEPTIDOMIMETICS

[75] Inventors: Ralph Hirschmann, Blue Bell; Ellen Leahy; Paul Sprengeler, both of Philadelphia, all of Pa.

[73] Assignee: Trustees of the University of Pennsylvania, Philadelphia, Pa.

[21] Appl. No.: 806,048

[22] Filed: Dec. 12, 1991

[51] Int. Cl.$^5$ .................. A61K 31/40; A61K 31/405; C07D 209/04
[52] U.S. Cl. ..................... 514/414; 514/415; 548/455; 548/469
[58] Field of Search ............... 548/455, 469; 514/414, 514/415

[56] References Cited

FOREIGN PATENT DOCUMENTS 89122396.8  6/1990  European Pat. Off. .

OTHER PUBLICATIONS

Sherman and Spatola, *J. Am. Chem. Soc.*, 112, 1990, 433.
Veber and Hirschmann, et al., *Proc. Natl. Acad. Sci. USA*, 1978 75 2636.
Thorsett, et al., *Biochem. Biophys. Res. Comm.*, 1983 111 166.
Veber and Hirschmann, et al., *Life Sciences*, 1984, 34, 1371.
Veber and Hirschmann, et al., *Nature*, 1981, 292.
Raynor and Reisine, *Journal of Pharmacology and Experimental Therapeutics*, 1989, 251;2, 510.
Reisine, et al., *Brain Research*, 1979, 177, 241.

*Primary Examiner*—Mary C. Lee
*Assistant Examiner*—Joseph K. McKane
*Attorney, Agent, or Firm*—Woodcock Washburn Kurtz Mackiewicz & Norris

[57] ABSTRACT

Compounds are provided which are crossreactive with peptides such as those bound by G-protein-linked receptors, together with preparative and therapeutic methods therefor. The compounds have the general structure:

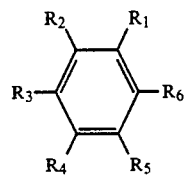

wherein at least one of $R_1$, $R_2$, $R_3$, $R_4$, $R_5$ or $R_6$ comprises a chemical functional group which causes the compounds to be crossreactive with the peptide of interest.

12 Claims, No Drawings

AROMATIC PEPTIDOMIMETICS

FIELD OF THE INVENTION

This invention relates to synthetic compounds which mimic or inhibit the biological and/or chemical activity of peptides, including compounds which are bound by G-protein-linked receptors.

BACKGROUND OF THE INVENTION

Peptides are implicated in a wide variety of biochemical processes in humans and other mammals. For example, it is known that a number of hormones and neurotransmitters are controlled by receptor-mediated stimulation of one or more of a family of guanine nucleotide-binding regulatory proteins, known as G-proteins. G-proteins activate or inhibit different effector enzymes, modulating the levels of intracellular secondary messengers. At least 50 sub-types of G-protein-linked receptors have been identified, among them the $\alpha$-adrenergic, $\beta$-adrenergic, muscarinic, cholinergic, dopamine, histamine, adenosine, serotonin, prostaglandin, leukotriene, thromboxane, prostacyclin, PAF, cAMP, enkephalin, endorphin, cholecystokinin, bombesin, substance K, substance P, neuromedin, bradykinin, FMLP, C5a, C3a, vasopressin, oxytocin, angiotensin, VIP, parathyroid hormone, calcitonin, neurotensin, TRH, somatostatin, rhodopsin, epinephrine, norepinephrine, acetylcholine, 5-hydroxytryptamine, thyrotropin, thyrotropin releasing-hormone, follicle stimulating, lutropin, choriogonadotropin, thrombin, retinal, and olfactory receptors. Nine or more G-proteins and at least seven effector systems have also been described. All of the G-protein-linked receptors analyzed to date contain from one to three potential sites of asparagine-linked glycosylation. The transmembrane signaling pathway used by G-protein-linked receptors represents one of the major mechanisms of signal transduction in cellular systems.

To date, there have been limited therapeutic applications involving peptides, due in considerable part to lack of oral bioavailability and to proteolytic degradation. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely an important contributing factor. The problem is, however, more complicated, because it has been recognized that even small, cyclic peptides which are not subject to rapid metabolic inactivation nevertheless exhibit poor oral bioavailability. This likely is due to poor transport across the intestinal membrane and rapid clearance from the blood by hepatic extraction with subsequent excretion into the intestine. These observations suggest that multiple amide bonds may interfere with oral bioavailability.

The design of peptide mimics which are resistant to degradation by proteolytic enzymes has become of increasing interest to peptide chemists, both for hormone agonist/antagonist and for enzyme inhibitor design. A primary goal has been to reduce the susceptibility of mimics to cleavage and inactivation by peptidases. In one approach, such as disclosed by Sherman and Spatola, *J. Am. Chem. Soc.*, 112, 1990, 433, one or more amide bonds have been replaced in an essentially isosteric manner by a variety of chemical functional groups. This stepwise approach has met with some success in that active analogs have been obtained. In some instances, these analogs have been shown to possess longer biological half-lives than their naturally-occurring counterparts. Nevertheless, this approach has limitations. Successful replacement of more than one amide bond has been rare. Consequently, the resulting analogs have remained susceptible to enzymatic inactivation elsewhere in the molecule. Moreover, this approach does not permit generalizations between chemically unrelated peptides concerning permissible amide mimic substitutions.

In another approach, a variety of uncoded or modified amino acids such as D-amino acids and N-methyl amino acids have been used to modify mammalian peptides. Alternatively, a presumed bioactive conformation has been stabilized by a covalent modification, such as cyclization or by incorporation of $\gamma$-lactam or other types of bridges. See, e.g., Veber and Hirschmann, et al., *Proc. Natl. Acad. Sci. USA*, 1978 75 2636 and Thorsett, et al., *Biochem. Biophys. Res. Comm.*, 1983 111 166. The primary purpose of such manipulations has not been to avoid metabolism or to enhance oral bioavailability but rather to constrain a bioactive conformation to enhance potency or to induce greater specificity for a receptor subtype.

Another approach, disclosed by Rich, D. H. in *Protease Inhibitors*, Barrett and Selveson, eds., Elsevier (1986), has been to design peptide mimics through the application of the transition state analog concept in enzyme inhibitor design. For example, it is known that the secondary alcohol of statine mimics the tetrahedral transition state of the scissile amide bond of the pepsin substrate. Again, increased potency rather than decreased susceptibility to peptidases or increased bioavailability was the principal objective. Moreover, the transition state analog concept has no apparent relevance to hormone agonist/antagonist design.

European Patent Application No. 89122396.8 disclosed benzoic acid and phenylacetic acid derivatives having structure (1).

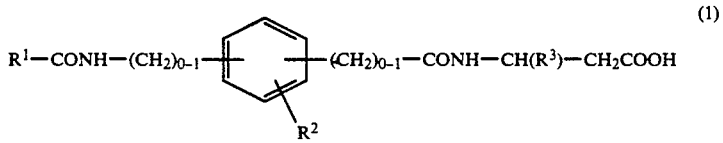

(1)

These compounds were said to inhibit the binding of fibrinogen, fibronectin and willebrand factor to the fibrinogen receptor of platelets as well as the binding of these and other adhesive proteins to the corresponding receptors on the surface of various cell types.

Accordingly, there remains a long-felt need for metabolically stable chemical compounds which exhibit both good bioavailability and the capacity to be bound by a variety of G-protein-linked receptors.

OBJECTS OF THE INVENTION

It is one object of the present invention to provide compositions of matter which mimic or inhibit the biological and/or chemical activity of peptides.

It is another object to provide compositions which are chemically more stable than naturally-occurring peptides, particularly under conditions such as found in the human body.

It is a further object to provide compositions which function as hormone agonists or hormone antagonists.

It is a further object to provide compositions which effectively are bound by G-protein-linked receptors.

It is still a further object to provide prophylactic, diagnostic, and therapeutic uses for peptide analogs.

SUMMARY OF THE INVENTION

These and other objects are accomplished by the present invention, which provides compounds, known as peptide analogs, which contain no peptide bonds yet which mimic or inhibit the chemical and/or biological activity of peptides. In general, the peptide analogs of the invention have structure (2):

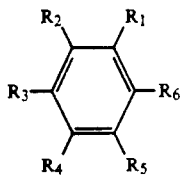

wherein at least one of $R_1$, $R_2$, $R_3$, $R_4$, $R_5$ or $R_6$ comprises a chemical functional group which causes the compounds to be crossreactive with the peptide of interest.

The peptide analogs of the invention can be employed to mediate the chemical and/or biological effects of hormone agonists/antagonists or other peptides. These compounds are believed to possess beneficial properties such as increased half-life, lack of immunogenicity, and the ability to cross the blood-brain barrier; they are believed to be useful for the development of pharmaceutical, therapeutic, and diagnostic techniques. Accordingly, the invention also provides methods for producing a prophylactic or therapeutic response in a mammal by administering to the mammal a pharmaceutically effective amount of one or more peptide analogs of the invention. In accordance with preferred embodiments, the present invention provides methods for producing such responses by modulating the activity of at least one mammalian G-protein-linked receptor by administering an effective amount of one or more peptide analogs of the invention.

DETAILED DESCRIPTION OF THE INVENTION

Non-peptide compounds which mimic or inhibit the chemical and/or biological activity of a variety of peptides can be produced by appending to certain core species such as the cyclohexane core of structure (2) chemical functional groups which cause the compounds to be at least partially crossreactive with the peptide. As will be recognized, compounds which mimic or inhibit peptides are to varying degrees crossreactive therewith. In accordance with the present invention, crossreactive moieties are those which compete with one another in binding G-protein-linked receptors through one of the many chemical reaction phenomena known in the art such as, for example, complexation, crystallization, or ionic, hydrogen, or covalent bonding. Thus, it is intended that the term "crossreactive" include both agonism and antagonism. Those skilled in the art recognize that a substance which competes with a peptide ligand in cell receptor binding is described as an agonist if the response of the cell is the same as or mimics the action of the peptide ligand. A substance that competes with the peptide ligand in receptor binding is referred to as antagonist if it blocks or inhibits the action of the cell to the action of the ligand.

There exist a wide variety of useful analytical techniques for elucidating the precise structure of a peptide. These techniques include amino acid sequencing, x-ray crystallography, mass spectroscopy, nuclear magnetic resonance spectroscopy, computer-assisted molecular modeling, peptide mapping, and combinations thereof. Structural analysis of a peptide generally provides a large body of data which in preferred embodiments comprises the amino acid sequence of the peptide as well as the three-dimensional positioning of its atomic components. It is believed that only certain of these components, which are known both individually and collectively as chemical functionality, participate in any given reaction phenomena. It will be appreciated that the participation of a chemical functional group in peptide reactivity is manifested by the linkage or coordination of the functional group with at least a portion of a complementary reactive moiety such as a hormone receptor. Such linkage or binding may be effected through a covalent, ionic, or hydrogen bond or some weaker atomic coordination effect such as complexation or crystallization.

In accordance with the present invention, peptide chemical functionality which participates in binding is identified by one of the many techniques known in the art. For example, such identification can be effected through a stepwise process wherein one or more peptide analogs are prepared. For example, peptide analogs having structure (2) can be prepared by substitution at certain of the positions $R_1$–$R_6$ with chemical functionalities which are crossreactive with functionalities found in the peptide. The activity of the analog in a binding assay is then compared with that of the peptide. The degree to which the binding of the analog corresponds with that of the peptide indicates the degree to which the substituents participate in the binding phenomena. Accordingly, one important criterion in preparing peptide analogs according to the present invention is the respective chemical similarity of the side chains found in the peptide and any potential substitutes therefor appended to the core structure in the analog. In general, it is desired that the chemical functional group in the peptide of interest and its substitute in at least one of the peptide analogs be somewhat chemically dissimilar. Where the substitute is chemically dissimilar from the peptide side chain, it will generally be easier to elucidate the contribution, if any, of side chain to activity of the peptide. For example, it is believed that the bioactive conformation of somatostatin (also known as somatotropin release inhibiting factor or SRIF) includes a β-turn involving residues 7–10 ($Phe^7$-$Trp^8$-$Lys^9$-$Thr^{10}$). These four amino acids have been shown to be necessary and sufficient for receptor recognition and activation, so long as they are held in the proper orientation. Somatostatin accomplishes this proper orientation through its ten remaining amino acids and the cystine bridge contained therein. In a number of active cyclic hexapeptide analogs for sometostatin, proper orientation of the four amino acids is maintained via dipeptide segments. For example, the cyclic hexapeptide I-363,301 (structure (3a)), disclosed by Veber and Hirschmann, et. al., *Life Sciences*, 1984, 34, 1371 and the cyclic hexapeptide MK-678 (structure (3b)), disclosed by Veber and Hirschmann, et. al., *Nature*, 1981, 292, accomplish the proper orientation via the segments Phe—N—Me—Ala or Phe—Pro, respectively.

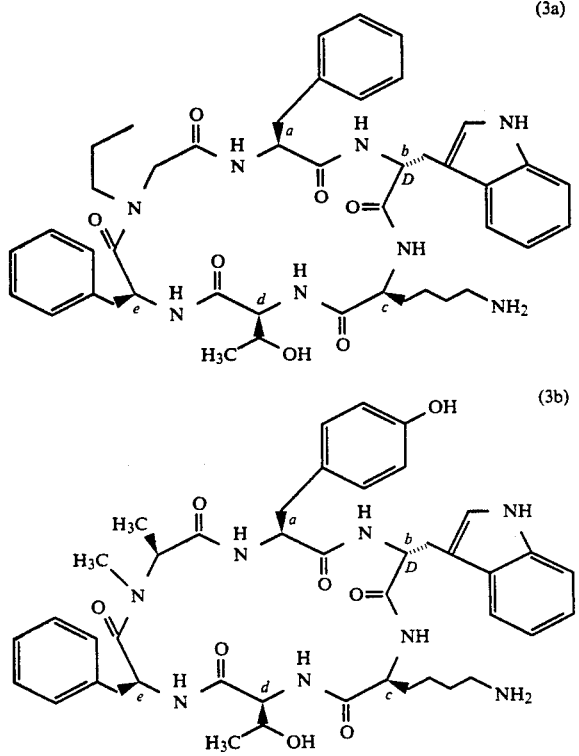

It is believed that the solution conformation of somatostatin involves a type I β-turn for residues 7-10 and that of the significantly more potent D-TRP diastereomer involves a type II' β-turn. While these two turns differ in the Φ and Ψ angles of the amide backbone, they are believed to assume similar orientations of the side chains at the receptor. In the cyclic hexapeptides, the Phe—N—Me—Ala sequence and the Phe-Pro sequence are believed to be part of a type VI β-turn. Of particular significance is the high activity found for a modified retro-enantiomeric cyclic hexapeptide wherein the amide backbone is reversed. This demonstrates that proper side chain topography is important for activity but that the amide backbone may not be.

In accordance with the present invention, peptide analogs having structure (2) are further simplified by including only three adjacent side chains of the four amino acids of the β-turn. These side chains are attached to rigid frameworks devoid of peptide bonds. The frameworks were developed through molecular modeling to orient the side chains appropriately and/or to permit the receptor to induce the proper fit.

While a proper β-turn requires the fourth amino acid of the β-turn—Thr in somatostatin and several cyclic hexapeptides and Val in the superactive cyclic hexapeptide —it is believed that neither the Thr nor the Val side chains are required for binding. This assumption is based on the fact that highly active somatostatin analogs are known which have either Val, Thr, Ser, α-aminobutyric acid, or Gly in the fourth position of the β-turn. Such non-specificity suggests a conformational rather than a binding role for that amino acid of the β-turn.

The phenylalanine residue in the dipeptide segments Phe-N-Me-Ala or Phe-Pro appears to add an important hydrophobic binding element. For this reason, the present synthetic analogs of somatostatin contain a corresponding aromatic residue. Increased hydrophobicity also should prove helpful in improving the duration of action and activity via oral administration of such compounds.

It is now believed that for the L-363,301 hexapeptide, structure (3a), the β-turn is important and the three groups extending from carbons a, b, and c—benzyl, indole, and alkylamino, respectively—are necessary for binding. Whereas the substituent at carbon d appears to be required to stabilize the β-turn rather than be required for binding, a benzyl group attached at carbon e of the skeleton is believed to be an important binding ligand which improves the activity of analogs. It has now been discovered that a new class of therapeutic agents can be formulated having activity in a broad spectrum of utilities, especially those related to the G-protein-linked receptors.

In accordance with the present invention, chemical functionality which participates in binding G-protein linked receptors includes any of the wide variety of functional groups known in the art. The side chains of naturally-occurring amino acids provide examples of suitable participatory functionality. Representative participatory chemical functionality which may be contained within groups $R_1$-$R_6$ is set forth in Table 1. For example, one or more of $R_1$-$R_6$ can have the structure A—(CH$_2$)y— or Z—O—, where y is from 0 to about 5 and Z is one of the side chains of Table 1.

TABLE 1

CH$_3$—
HO—CH$_2$—
C$_6$H$_5$—CH$_2$—
HO—C$_6$H$_5$—CH$_2$—

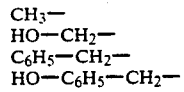

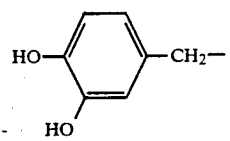

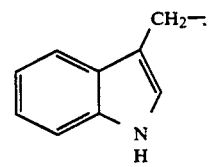

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—HO—CH$_2$—CH$_2$—
HO$_2$C—CH$_2$—CH$_2$

TABLE 1-continued

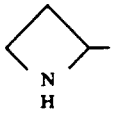

HCO₂—CH₂—CH₂—
NH₂C(O)—CH₂—CH₂—
(CH₃)₂—CH—
(CH₃)₂—CH—CH₂—
CH₃—CH₂—CH₂—
H₂N—CH₂—CH₂—CH₂—
H₂N—C(NH)—NH—CH₂—CH₂—CH₂—
H₂N—C(O)—NH—CH₂—CH₂—CH₂—
CH₃—CH₂—CH(CH₃)—
CH₃—CH₂—CH₂—CH₂—
H₂N—CH₂—CH₂—CH₂—CH₂—

In accordance with the present invention, non-peptide analogs preferably possess the general structure (2):

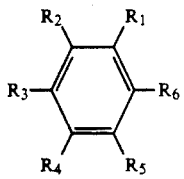

(2)

wherein:

$R_1$ is —CH₂OCH₂)$_n$R$_A$, —CH₂OC(O) (CH₂)$_n$R$_A$, —(CH₂)$_n$R$_A$, or —CH₂C(O) (CH₂)$_n$R$_A$, where R$_A$ is —H, alkyl or alkenyl having from about 1 to about 14 carbon atoms and up to about 4 nitrogen atoms, or aryl having from about 6 to about 14 carbon atoms and up to about 4 nitrogen atoms, and n is an integer from to about 12;

at least one of $R_2$, $R_3$, and $R_4$, independently, is —CH₂O(CH₂)$_m$R$_B$, —CH₂OC(O) (CH₂)$_m$R$_B$, —(CH₂)$_m$R$_B$ or —CH₂C(O) (CH₂)$_m$R$_B$ where R$_B$ is —H or aryl having from about 6 to about 14 carbon atoms, and m is an integer from 0 to about 5;

$R_5$ is —CH₂O(CH₂)$_p$NHR$_C$, —CH₂OC(O) (CH₂)$_p$NHR$_C$, —CH₂O(CH₂)$_p$R$_D$, —CH₂OC(O) (CH₂)$_p$R$_D$, —(CH₂)$_p$NHR$_C$, —CH₂C(OH) (CH₂)$_p$NHR$_C$, —(CH₂)$_p$R$_D$ or —CH₂C(O) (CH₂)$_p$R$_D$, where p is an integer from 0 to about 10;

$R_C$ is —R$_E$ or —C(O)R$_E$;

$R_D$ is —H, —OR$_E$, or —C(O)R$_E$;

$R_E$ is —H, alkyl or alkenyl having from about 1 to about 14 carbon atoms and up to about 4 nitrogen atoms, or aryl having from about 6 to about 14 carbon atoms and up to about 4 nitrogen atoms; and $R_6$ is —H or —OH;

or a pharmaceutically acceptable salt thereof.

It will be understood that the terms "alkyl" and "alkenyl" as employed herein are intended to include cyclic as well as straight chain moieties.

As will be recognized, the precise identity of $R_1$-$R_6$ depends intimately upon the peptide of interest whose biological and/or chemical activity is to be mimicked or inhibited. For example, in the case of compounds which are bound by G-protein-linked receptors such as the substance P receptor, $R_A$ should be an aryl functional group, preferably an nitrogen-substituted aryl group such as pyridine or indole. More preferably, $R_A$ is a 3-substituted indole. For such compounds, n should be 2 and $R_B$ should be phenyl. The integer m should be zero or, preferably, 1. Also, $R_5$ should be —O(CH₂)$_p$NH₂ or —O(CH₂)$_p$NHR$_C$, where p is from about 2 to about 8, preferably 3 to about 6, more preferably 5. $R_C$ can be, for example, a phenyl, benzyl or nitrogen heterocyclic moiety. Where substitution is possible at more than one position of these and other $R_C$, it is intended that the present invention include each of resulting peptide analogs. For example, it is intended that the invention include analogs wherein $R_C$ is a pyridine or isonicotinic acid residue having one of the following structures:

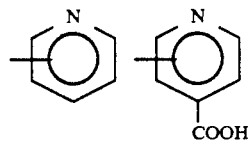

Preferably, however, $R_C$ is —C(O)CH₃.

One preferred peptide analog has structure (3), wherein Bn=benzyl.

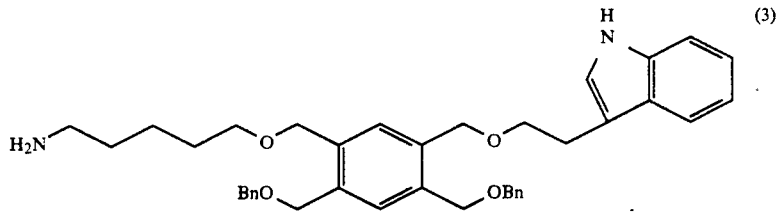

(3)

Peptide analogs of the invention are preferred to the extent that they selectively and effectively are bound by G-proteins-linked receptors such as the somatostatin receptor, the β-adrenergic receptor, and the substance P receptor. It will be recognized that the degree to which a compound is bound by a receptor is known as its binding activity or potency. The potency of a compound commonly is expressed as its inhibitory concentration (IC), the concentration at which the compound is able to displace a predetermined portion—typically 50%—of another compound which is already bound by a particular receptor. In the case of ligand-binding studies, the compound that is displaced is a radioactive agonist or antagonist at the receptor under study. It is preferred in accordance with the present invention that a peptide analog possess a clinically effective IC$_{50}$ in at least one mammal; that is, it should possess an IC$_{50}$ which is low enough to inhibit binding of radioactive agonist or antagonist to a given G-protein linked receptor while causing a minimum of unacceptable side effects in the mammal. As will be recognized, clinically effective inhibitory concentrations vary depending on a number of factors, such as the pharmacokinetic characteristics and stability of the compound under study and thus must be determined empirically for each analog and each factor. For example, the clinically effective concentration for the somatostatin receptor is about 50-500 nM, but for the in vitro system the potency is about 1-10 nM. In general, it is desired that the potency of a compound of the invention be as great as possible, preferably greater than or equal to the native hormone.

Selectivity or specificity is manifested for a compound of the present invention by its tendency to be bound by one particular G-protein-linked receptor but not other G-protein-linked receptors. In an experimental context, selectivity is manifested where a compound is bound by a particular receptor when placed in contact or close proximity with a medium containing at least one other receptor. Typically, specificity is expressed as a ratio of the potency or activity of a compound for two different receptors. Thus, a compound having an $IC_{50}$ of 100 μm for compound A and $IC_{50}$ of 200 μM for compound B can be said be two times more selective for compound A. In general, the selectivity of the peptide analogs of the present invention should be as great as possible. Selectivities greater than about 50-100 fold are preferred and selectivities greater than about 500 fold even more preferred.

As can be seen, the present invention provides a wide variety of peptide analogs which effectively and selectively are bound by individual G-protein-linked receptors. The peptide analogs which bear amino groups are capable of forming salts with various inorganic and organic acids and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts may be formed by conventional means, such as by reacting the free base form of the product with one or more equivalents of the appropriate acid in a solvent or medium in which the salt is insoluble, or in a solvent such as water which is later removed in vacuo or by freeze drying. The salts also may be formed by exchanging the anions of an existing salt for another anion on a suitable ion exchange resin.

The present invention also provides compositions which comprise one or more peptide analogs. To the extent that the compositions comprise individual peptide analogs which are bound by certain receptors, the compositions will likely also be bound by the same receptors. The analogs themselves may be present in the compositions in any of a wide variety of forms. For example, two or more peptide analogs may be merely mixed together or may be more closely associated through complexation, crystallization, or ionic or covalent bonding.

Those skilled in the art will appreciate that a wide variety of prophylactic, diagnostic, and therapeutic treatments may be prepared from the synthetic compounds and compositions of the invention, due in large part to the crossreactivity—that is, agonism or antagonism—of these moieties with one or more naturally-occurring peptides. For example, by administering an effective amount of a peptide analog, prophylactic or therapeutic responses can be produced in a human or some other type mammal. Preferred responses are produced by modulating—that is, increasing, decreasing or otherwise modifying—the activity of at least one G-protein-linked receptor. It will be appreciated that the production of prophylactic or therapeutic responses includes the initiation or enhancement of desirable responses, as well as the cessation or suppression of undesirable responses.

Compositions for use in the methods of this invention can be in the form of a solid, semisolid or liquid form and can include one or more of peptide analogs as an active ingredient in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes maybe used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of said compounds in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

A compound of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds within the present invention on the order from about 0.01 mg to about 50 mg per kilogram of body weight per day, preferably from about 0.1 mg to about 10 mg per kilogram body weight per day, are believed to be useful in the treatment of the above-indicated conditions (i.e., from about 0.7 mg to about 3.5 g per patient per day, assuming a 70 kg patient). In addition, the compounds of the present invention may be administered on an intermittent basis; i.e. at semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 mg of active agent compounded with an appropriate and convenient amount of carrier material which may vary from about 5 to about 95 percent of the total composition. Dosage unit forms will generally contain from about 0.5 mg to about 500 mg of active ingredient. For topical administration in larger mammals a preparation containing a 1–3% concentration of active agent may be utilized.

It will be understood, however, that the specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day.

Additional objects, advantages, and novel features of this invention will become apparent to those skilled in the art upon examination of the following examples thereof, which are not intended to be limiting.

EXAMPLE 1

Preparation of Analog Having Structure (3)

A solution of 1,2,4,5-tetraformylbenzene (10.0 grams, 52.6 mmol) in 10N potassium hydroxide (250 mL) is stirred at room temperature for 5 hours. The reaction is acidified to Ph 2 and heated for 20 minutes. Upon cooling, a white precipitate forms. Filtration and recrystallization from ethanol yields pure structure (4).

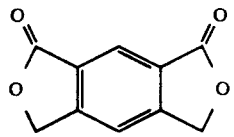
(4)

To a solution of (4) (10.0 grams, 52.2 mmol) in toluene (100 mL) at −78° C. is added diisobutylaluminum hydride (1M in toluene, 109.5 mL, 109.5 mmol). The solution is stirred at −78° C. for 1 hour and then at room temperature for 30 minutes. The reaction is diluted with methanol (25 mL) and washed with aqueous sodium potassium tartrate. The organic layer is separated, washed with water, dried over anhydrous sodium sulfate and concentrated under reduced pressure. Purification by flash column chromatography yields pure structure (5).

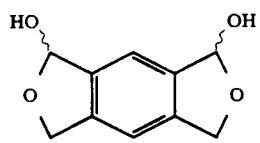
(5)

To a suspension of sodium hydride (2.3 grams, 56.7 mmol) in dry tetrahydrofuran (THF; 25 mL) at 0° C. is added a solution of (5) (5.0 grams, 25.8 mmol) in dry THF (50 mL). The reaction is stirred at room temperature for 1 hour. The reaction is cooled to 0° C. and to it is added benzyl bromide (6.7 mL, 56.7 mmol) followed by a catalytic amount of tetrabutylammonium iodide (0.25 grams). The reaction is stirred at room temperature for 24 hours followed by quenching with ammonium chloride solution. The resulting mixture is extracted with dichloromethane, the organic layer washed with a saturated sodium chloride solution, dried over anhydrous sodium sulfate and concentrated to yield an oil. Purification by flash column chromatography yields pure structure (6) (Bn =benzyl).

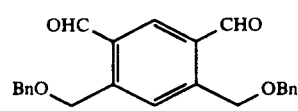
(6)

To a solution of (6) (5.0 grams, 13.4 mmol) in ethanol 50 mL) at 0° C. is added sodium borohydride (1.1 grams, 29.4 mmol). The reaction is stirred at room temperature overnight. Water is added to quench excess NaBH4. The solvents are removed under reduced pressure and the residue taken up in a small amount of water. The aqueous solution is extracted with dichloromethane and the organic layer dried over anhydrous sodium sulfate. Concentration yields an oil (structure (7) which is purified by flash column chromatography.

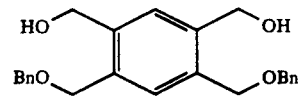
(7)

To a solution of 5-aminopentanol (5.0 grams, 48.5 mmol) in benzene (150 mL) is added N-carbethoxyphthalimide (11.0 grams, 50.2 mmol). The solution is stirred at room temperature for 5 hours. The solvent is removed under reduced pressure to yield an oil which is purified by flash column chromatography. To a solution of the phthalimidoalcohol (5.0 grams, 21.4 mmol) in dry dichloromethane (50 mL) at 0° C. is added 2,6-di-tert-butyl-4-methylpyridine (4.9 grams, 23.5 mmol) followed by triflic anhydride (4.0 mL, 23.5 mmol). The reaction is stirred at room temperature for 20 minutes, after which it is poured into water and extracted with dichloromethane. The organic layer is dried over anhydrous sodium sulfate and concentrated under reduced pressure. The triflate (structure (8), Tf=trifluoromethanesulfonate) is used immediately in the next reaction without further purification.

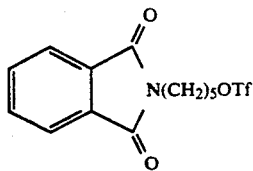

To a solution of (8) (5.0 grams, 15.0 mmol) in dry dichloromethane (100 mL) at 0° C. is added 2,6-di-tert-butyl-4-methylpyridine (3.4 grams, 16.5 mmol), followed by a solution of (7) (5.7 grams, 15.0 mmol) in dry dichloromethane (100 mL). To this cooled solution is added sodium hydride (0.60 grams, 15.0 mmol). The resulting reaction mixture is stirred at room temperature for 24 hours. The reaction is quenched by addition of ammonium chloride solution and extracted with dichloromethane. The organic layer is washed with saturated sodium chloride solution, dried over anhydrous sodium sulfate and concentrated under reduced pressure. The product (structure (9)) is purified by flash column chromatography.

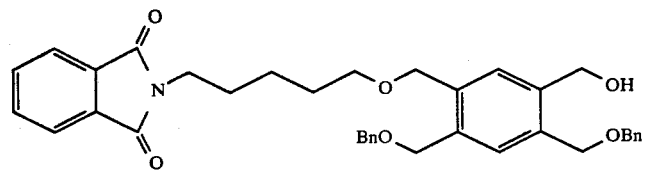

To a suspension of sodium hydride (0.37 grams, 9.3 mmol) in dry THF (25 mL) at 0° C. is added a solution of (9) (5.0 grams, 8.4 mmol) in dry THF (i00 mL). The reaction is stirred at room temperature for 1 hour. The reaction is then cooled to 0° C. and to it is added a solution of N-phenylsulfonyltryptophol bromide (3.4 grams, 9.3 mmol) in dry THF (25 mL). The solution is stirred at room temperature for 24 hours. The reaction is quenched by addition of aqueous ammonium chloride and extracted with dichloromethane. The organic layer is dried over anhydrous sodium sulfate and concentrated to yield an oil. Purification by flash column chromatography affords pure structure (10) (Ph=phenyl).

duced pressure. The resulting crude product (structure (3)) is purified by flash column chromatography.

EXAMPLE 2

The affinity of compounds of the invention for the substance P receptor is determined employing the following procedure.

A. Receptor Expression in COS

To express the cloned human neurokinin-1 receptor (NK1R) transiently in COS, the cDNA for the human NK1R was cloned into the expression vector pCDM9 which was derived from pCDM8 (Invitrogen) by inserting the ampicillin resistance gene (nucleotide 1973 to 2964 from Bluescript SK+) into the Sac II site. Transfection of 20 μg of the plasmid DNA into 10 million COS cells was achieved by electroporation in 800 μl of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 nM glucose, 10 mM HEPES pH 7.4) at 260 V and 950 μF using the IBI Genezapper (IBI, New Haven, Conn.). The cells were incubated in 10% fetal calf serum, 2 mM glutamine, 100 U/ml penicillin-streptomycin, and 90% DMEM media (Gibco, Grand Island, N.Y.) in 5% CO$_2$ at 37° C. for three days before the binding assay.

B. Assay Protocol using COS

The binding assay of human NK1R expressed in COS cells is based on the use of $^{125}$I-substance P ($^{125}$I-SP, from DuPont, Boston, Mass.) as a radioactively labeled ligand which competes with unlabeled substance P or any other ligand for binding to the human NK1R. Monolayer cell cultures of COS were dissociated by the non-enzymatic solution (Specialty Media, Lavallette, N.J.) and resuspended in appropriate volume of the binding buffer (50 mM Tris pH 7.5, 5 mM MnCl$_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to

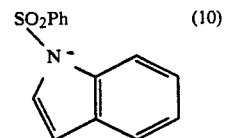

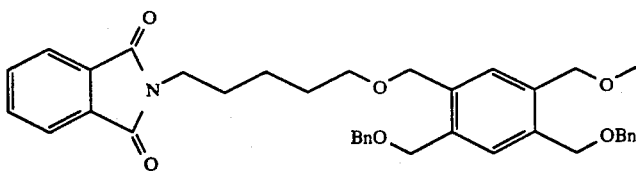

To a solution of (10) (5.0 grams, 5.7 mmol) in methanol (100 mL) is added sodium methoxide (1.54 grams, 28.5 mmol) and the reaction mixture heated to reflux for 24 hours. The solvents are removed under reduced pressure to yield a residue which is diluted with water and extracted with dichloromethane. The organic layer is washed with saturated sodium chloride solution, dried over sodium sulfate and concentrated under reabout 10,000 cpm of specific $^{125}$I-SP binding (approximately 50,000 to 200,000 cells). In the binding assay, 200 μl of cells were added to a tube containing 20 μl of 1.5 to 2.5 nM of $^{125}$I-SP and 20 μl of unlabeled substance P or any other test compound. The tubes were incubated at 4° C. or at room temperature for 1 hour with gentle shaking. The bound radioactivity was separated from unbound radioactivity by GF/C filter (Brandel, Gaithersburg, Md.) which was pre-wetted with 0.1 polyethylenimine. The filter was washed with 3 ml of wash buffer (50 Tris pH 7.5, 5 mM $MnCl_2$, 150 mM NaCl) three times and its radioactivity was determined by gamma counter.

A variety of compounds are tested according to the COS cell procedure. The concentration of compound required to inhibit the binding of substance P to the human neurokinin-1 receptor by 50% is measured.

It will be recognized that the affinity of a variety of compounds for the SRIF receptor can be determined by studying the displacement of $^{125}I$-CGP-23996 from AtT-20 cells using a method generally in accordance with that disclosed by Raynor and Reisine, *Journal of Pharmacology and Experimental Therapeutics*, 1989, 251; 2, 510. Similarly, the affinity of a variety of compounds for other G-protein-linked receptors can be determined by studying the displacement of a variety of radioligands from AtT-20 and brain cells using the method generally disclosed by Reisine, et al., *Brain Research*, 1979, 177, 241.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the structure:

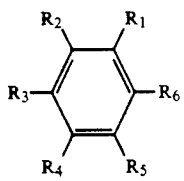

$R_1$ is $-CH_2O(CH_2)_nR_A$, where $R_A$ is heteroacryl having from about 6 to about 14 carbon atoms and one nitrogen atom, and n is an integer from 0 to about 2;

$R_2$, $R_3$, and $R_4$, independently, are $-H$ or $-CH_2O(CH_2)_mR_B$, where $R_B$ is aryl having from about 6 to about 14 carbon atoms, and m is an integer from 0 to about 5, provided that at least one of $R_2$, $R_3$, and $R_4$ is $-CH_2O(CH_2)_mR_B$;

$R_5$ is $-CH_2O(CH_2)_pNHR_C$, where:
p is an integer from 2 to about 8;
$R_C$ is $-R_E$ or $-C(O)R_E$;
$R_E$ is $-H$, alkyl or alkenyl having from about 1 to about 14 carbon atoms and up to about 4 nitrogen atoms, or aryl having from about 6 to about 14 carbon atoms; and $R_6$ is $-H$ or $-OH$;

or a pharmaceutically acceptable salt thereof.

2. The compound of claim 1 wherein $R_A$ is indole.
3. The compound of claim 1 wherein $R_A$ is 3-indole.
4. The compound of claim 1 wherein $R_B$ is phenyl.
5. The compound of claim 1 wherein m is 1.
6. The compound of claim 1 wherein p is from about 3 to about 6.
7. The compound of claim 1 wherein p is 5.
8. The compound of claim 1 wherein $R_5$ is $-CH_2O(CH_2)_5NH_2$.
9. The compound of claim 1 wherein $R_6$ is H.
10. The compound of claim 1 wherein $R_1$ is $-CH_2O(CH_2)_2(3$-indole); $R_2$ and $R_4$ are $-CH_2O-$benzyl; $R_3$ is H, $R_5$ is $-CH_2O(CH_2)_5NH_2$, and $R_6$ is H.

11. A method for modulating the activity of at least one mammalian G-protein-linked receptor, comprising administering to a mammal an effective amount of a compound having the structure:

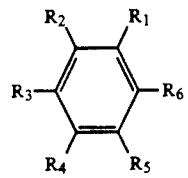

wherein:
$R_1$ is $-CH_2O(CH_2)_nR_A$, where $R_A$ is heteroacryl having from about 6 to about 14 carbon atoms and one nitrogen atom, and n is an integer from 0 to about 2;

$R_2$, $R_3$, and $R_4$, independently, are $-H$ or $-CH_2O(CH_2)_mR_B$, where $R_B$ is aryl having from about 6 to about 14 carbon atoms, and m is an integer from 0 to about 5, provided that at least one of $R_2$, $R_3$, and $R_4$ is $-CH_2O(CH_2)_mR_B$;

$R_5$ is $-CH_2O(CH_2)_pNHR_C$, where:
p is an integer from 2 to about 8;
$R_C$ is $-R_E$ or $-C(O)R_E$;
$R_E$ is $-H$, alkyl or alkenyl having from about 1 to about 14 carbon atoms and up to about 4 nitrogen atoms, or aryl having from about 6 to about 14 carbon atoms; and $R_6$ is $-H$ or $-OH$;

or a pharmaceutically acceptable salt thereof.

12. A method for mimicking or inhibiting the chemical activity of a peptide, comprising providing in place of the peptide at least one chemical compound having the structural:

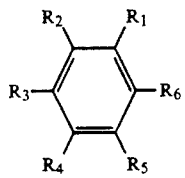

wherein:
$R_1$ is $-CH_2O(CH_2)_nR_A$, where $R_A$ is heteroaryl having from about 6 to about 14 carbon atoms and one nitrogen atom, and n is an integer from 0 to about 2;

$R_2$, $R_3$, and $R_4$, independently, are $-H$ or $-CH_2O(CH_2)_mR_B$, where $R_B$ is aryl having from about 6 to about 14 carbon atoms, and m is an integer from 0 to about 5, provided that at least one of $R_2$, $R_3$, and $R_4$ is $-CH_2O(CH_2)_nR_B$;

$R_5$ is $-CH_2O(CH_2)_pNHR_C$, where:
p is an integer from 2 to about 8;
$R_C$ is $-R_E$ or $-C(O)R_E$;
$R_E$ is $-H$, alkyl or alkenyl having from about 1 to about 14 carbon atoms and up to about 4 nitrogen atoms, or aryl having from about 6 to about 14 carbon atoms; and $R_6$ is $-H$ or $-OH$;

or a pharmaceutically acceptable salt thereof.

* * * * *